United States Patent [19]
Valentini et al.
[11] Patent Number: 4,786,281
[45] Date of Patent: Nov. 22, 1988

[54] DEVICE FOR CONNECTING ONE END OF A LIQUID MEDICAMENT DELIVERY CANNULA TO AN APPARATUS FOR CONNECTING A SYRINGE TO A VIAL CONTAINING THE MEDICAMENT

[75] Inventors: Luigi Valentini, Milan; Mario Coccia, Cesano Boscone, both of Italy

[73] Assignee: Farmitalia Carlo Erba S.p.A., Milan, Italy

[21] Appl. No.: 879,886

[22] Filed: Jun. 30, 1986

[30] Foreign Application Priority Data

Aug. 2, 1985 [IT] Italy .............................. 21857 A/85

[51] Int. Cl.[4] .............................................. A61M 5/005

[52] U.S. Cl. .................................... 604/256; 604/905; 604/167; 604/86

[58] Field of Search ................... 604/86, 256, 905, 88, 604/201, 206, 283, 167, 15, 127, 414, 415

[56] References Cited

U.S. PATENT DOCUMENTS

| | | | |
|---|---|---|---|
| 3,015,332 | 1/1962 | Brecht | 604/15 |
| 3,207,372 | 9/1965 | Evans | 604/127 |
| 3,709,365 | 1/1973 | Czaplinski et al. | 604/415 |
| 3,976,073 | 8/1976 | Quick et al. | 604/415 |
| 4,022,205 | 5/1977 | Tenczar | 604/905 |
| 4,030,494 | 6/1977 | Tenczar | 604/905 |
| 4,116,196 | 9/1978 | Kaplan et al. | 604/905 |
| 4,369,781 | 1/1983 | Gilson et al. | 604/905 |
| 4,445,896 | 5/1984 | Gianturco | 604/283 |
| 4,473,067 | 9/1984 | Schiff | 604/167 |
| 4,601,703 | 7/1986 | Herlitze | 604/86 |

FOREIGN PATENT DOCUMENTS

| | | | |
|---|---|---|---|
| 2067075 | 7/1981 | Fed. Rep. of Germany | 604/905 |

*Primary Examiner*—Stephen C. Pellegrino
*Assistant Examiner*—Colleen M. Reilly
*Attorney, Agent, or Firm*—Oblon, Fisher, Spivak, McClelland & Maier

[57] ABSTRACT

In order to withdraw pharmaceutical products from sterile vials by means of a syringe, apparatus is used on one end of which a syringe possibly containing a liquid solvent is mounted and at the other end of which a seat is provided for housing the mouth of a vial. The syringe needle can puncture the rubber or similar stopper by which the vial is sealed, while the needle itself remains enclosed and protected by said apparatus. The invention relates to a device which, when the vial has been removed, can itself be housed in said apparatus seat to enable the needle to puncture a rubber stopper provided on the device, which is connected to one end of a cannula having for example mounted on its other end a needle for transfusion purposes. In this manner, the liquid can be discharged from the syringe while the needle remains enclosed and protected by the said apparatus.

4 Claims, 1 Drawing Sheet

DEVICE FOR CONNECTING ONE END OF A LIQUID MEDICAMENT DELIVERY CANNULA TO AN APPARATUS FOR CONNECTING A SYRINGE TO A VIAL CONTAINING THE MEDICAMENT

BACKGROUND OF THE INVENTION

This invention relates to a device for connecting one end of a liquid medicament delivery cannula to an apparatus for connecting a syringe to a vial containing the medicament.

Medicaments exist which are preserved under sterile conditions in vials sealed by a rubber, silicone or similar stopper. The medicament is withdrawn from the vial by a syringe provided with a needle which punctures the rubber stopper, to penetrate into the vial. Often, the syringe is used to inject into the vial a liquid (solvent, physiological solution or the like) in which the medicament is dissolved or diluted inside the vial. The liquid together with the pharmaceutical substance dissolved in it is then drawn into the syringe for subsequent use.

Often, in order to avoid contaminating the needle and, in special cases, the environment (when very dangerous medicaments such as antitumoral medicaments are present) and thus to protect persons handling the syringe and vial from danger, special arrangements of various types must be used, the most simple of which is to fit on to the free end of the syringe an apparatus which surrounds and protects the needle. This apparatus comprises a seat into which the mouth of the vial can be inserted so that it remains secured to the apparatus. The syringe is then moved towards the vial so that the needle point punctures the rubber stopper of the vial. In this manner, the possible solvent can be fed into the vial and the medicament solution be drawn into the syringe under very safe conditions, because the needle, the vial stopper and any medicament droplets lie within a closed environment bounded by the said apparatus and, at its two ends, by the syringe and vial.

Apparatus of this type are described in U.S. Pat. Nos. 3,336,924, 3,826,260 and 3,995,630, in European published patent application No. 126,718 and in Italian published patent application No. 19785 A/84, corresponding to Belgian pat. No. 901,699. European patent application No. 126,718 and Italian patent application no. 19785 A/84 provide a sealing member (in correspondence with that seat of the apparatus which is to house the vial mouth), above which the point of the syringe needle is made to rise before the vial is removed from said apparatus. In this manner, even after the medicament has been drawn into the syringe, no contamination of the needle or of the external environment can take place because the needle is entirely housed within a closed chamber bounded by the apparatus, by the syringe and by said sealing member.

When the medicament is to be used, either the apparatus is removed from the syringe to thus leave the needle free (with all the dangerous contamination consequences which should have been avoided), or a device has to be inserted into the said apparatus seat to allow this apparatus to be directly connected to a discharge cannula for the medicament. The cannula can for example carry at its free end a needle (such as an epicranial needle) for transfusing the medicament into the vein directly from the syringe.

The possibility (whish is in effect a necessity) of using such a type of device fitted to one end of the cannula and fixable into said apparatus seat was described for the first time in Italian patent application no. 19785 A/84 and subsequently in European patent application No. 126,718.

In Italian patent application No. 19785 A/84, it states that the device mounted on the end of the cannula "has a profile completely analogous to that of the vial". It has been found in practice that it is impossible (especially for cost and space reasons) to give this device exactly the shape of the vial. However, if the device reproduces only the shape of the vial mouth (ie of that part provided with the rubber stopper and the relative ring which fixes it to the vial), the device very easily and very frequently penetrates with its axis inclined to the axis of the apparatus seat, with the result that the connection device can jam in the apparatus seat or penetrate only partially into it, so leaving an empty space between the rubber or similar stopper provided on the device and the sealing member provided in the apparatus in correspondence with the containing seat into which the device has been inserted. Medicament droplets can penetrate into and collect in this empty space when the syringe needle is lowered to pass through the sealing member of the apparatus and then through the rubber stopper of the device, with obviously dangerous consequences.

The device for connecting the medicament discharge cannula to the apparatus which protects the syringe needle as illustrated in European patent application No. 126,718 is of very complicated construction (and therefore practically unimplementable), as can be easily seen by examining FIG. 4 of this patent, in which the device is shown in section.

SUMMARY OF THE INVENTION

The main object of the present invention is to provide a device of the aforesaid type which is of extremely simple and economical construction and which in particular is conformed in such a manner as to always assume the required correct position in the seat of the apparatus into which it is inserted in order to allow delivery of the medicament by the syringe.

This and further objects are attained by a device comprising an elongate annular structure having two ends within which is positioned a tubular element extending between the ends. Profile means are provided at one of the ends for attachment of a cannula while a projecting collar extends radially outward from the other of the ends of the annular structure. An elastic stopper covers an end of the tubular element at the other end of the annular structure. At least three separate fins extend radially outward from the annular structure and extend longitudinally from the collar toward the one end, the radially outer edge of each of the fins being substantially aligned with a radially outer edge of the collar. This permits an apparatus which is otherwise used for connecting a syringe to a vial, to be connected to the collar and fins in a stable manner.

DETAILED DESCRIPTION OF THE DRAWINGS

The construction and characteristics of the device will be more apparent from the description given hereinafter of a preferred embodiment thereof with reference to the accompanying drawing in which.

Figure 2:
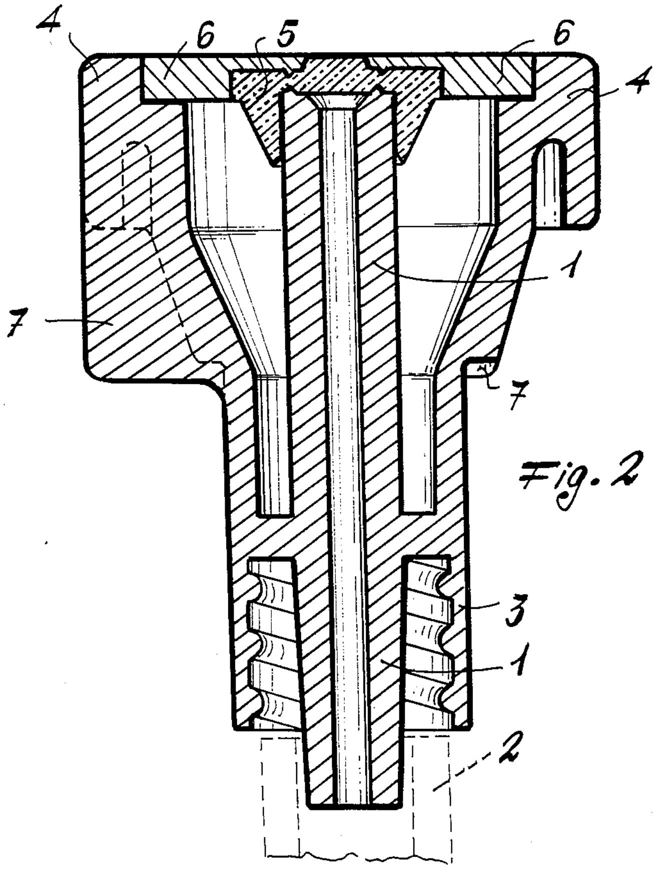
FIG. 2 is a longitudinal section through the device on the line II—II of FIG. 1.

The device shown on the drawings comprises an elongate profiled structure, along the centre of which there extends a thin longitudinal tubular element 1 open at its lower end (with respect to FIG. 2). The lower one end (ie the free end) of the tubular element 1 can constitute an appendix on which the free end of a cannula 2 (shown by dashed lines in FIG. 2) can be mounted, on its other end there being mounted a needle for transfusing the medicament into the vein.

In the illustrated embodiment, the lower free end of the tubular element 1 is surrounded by another tubular appendix 3, from the inner surface of which there projects a helical rib which can be used for the screwed fitting of a multi-way valve, which would be connected to the cannula 2 and also to a vessel containing for example a physiological solution, distilled water or another liquid. In any event, this multi-way valve does not form part of the present invention, and is therefore not described in detail. In correspondence with the free upper other end (FIG. 2) of the tubular element 1, there projects radially from the profiled structure a collar 4 having the same shape and size as the mouth of a normal vial of the type used for containing medicaments, in particular medicaments in powder form which are put into solution by a liquid injected into the vial through the needle of a syringe, this needle puncturing a rubber stopper which seals the vial mouth.

Figure 1:
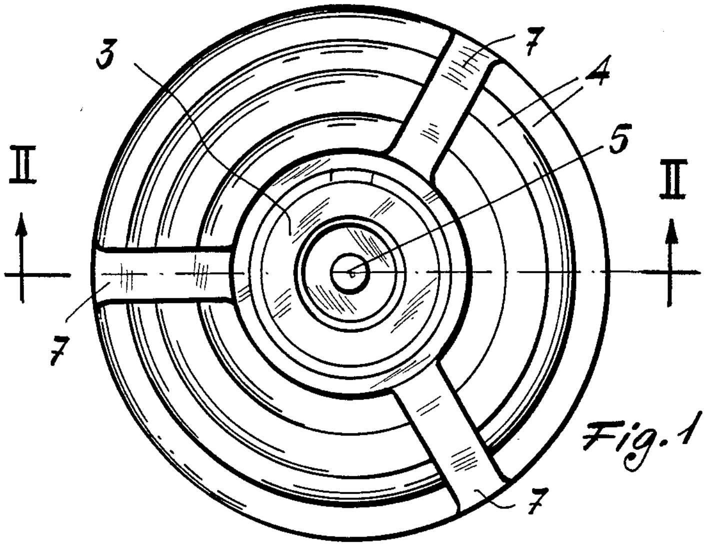
FIG. 1 is a view of the device from below (with respect to FIG. 2)

As can be seen in particular in FIG. 1, the upper end of the tubular element 1 is sealed by a rubber, silicone or similar stopper 5 which is retained and firmly pressed against the end of the element 1 by a retention ring 6 which is locked on to the profiled structure of the device.

Three fins 7, distrubuted 120° apart, project radially outwards from the profiled structure and extend longitudinally from the collar 4 towards the other end of the profiled structure. The radially outer free longitudinally edge of the fins 7 is aligned with the surface of the radially outer edge of the collar 4, as can be clearly seen from FIG. 2.

It will be assumed that the cannula 2 is connected to the free end of the tubular element 1 and to a needle for intravenous transfusion, and that the user of the described device holds in his hand a syringe containing a medicament in liquid form, and that an apparatus of the type described in the prior patents cited in the introductory part of the present description is mounted on said syringe. This apparatus covers and protects the needle, in the manner stated heretofore.

The free end of the device, ie the collar 4, is now inserted into the seat provided at the free end of the apparatus connected to the syringe, and becomes exactly contained in said seat because the collar is of the exact shape and size as the vial mouth on which the apparatus has been previously fitted to enable the medicament to be drawn into the syringe.

It should be noted that the purpose of the fins 7 is essentially to allow correct positioning of the device and its unhindered insertion into the apparatus seat, in that the outer free edges of the fins act as a guide for the device by resting against and sliding in contact with the inner cylindrical wall defining the apparatus seat.

When the device has been inserted into its correct position in the apparatus seat, the syringe is moved towards the device until the syringe needle punctures the stopper 5 and penetrates into the cavity of the tubular element 1. At this point, by pressing the syringe plunger, the medicament can be discharge directly into the vein by way of the needle, the cavity of the element 1 and the cannula 2.

It should be noted that the cavity of the element 1 is of very small diameter, so that in practice there exist no chambers in which droplets or consistent quantities of medicament can remain.

What is claimed is:

1. A device for connecting one end of a liquid medicament delivery cannula to an apparatus for connecting a syringe to a vial containing a medicament, comprising:
   - an elongate annular structure having two ends;
   - a tubular element positioned inside said annular structure and extending between said ends;
   - appendix means at one of said ends for attachment of a cannula;
   - a projecting collar extending radially outward from the other of said ends of said annular structure;
   - an elastic stopper covering an end of said tubular element at said other end of said annular structure; and
   - at least three separate fins extending radially outwardly from said annular structure and extending longitudinally from said collar toward said one end, the entirety of a radially outer edge of each of said fins being substantially aligned with a radially outer edge of said collar,
   - whereby said apparatus for connecting a syringe to a vial may be fitted on said collar and said fins with a cylindrical portion of said apparatus complementarily guided by contact with said collar and said fins.

2. A device as claimed in claim 1 comprising three of said fins angularly distributed 120° apart.

3. A device as claimed in one of claims 1 and 2, including a retention ring fixed to said structure and locking said stopper on said annular structure.

4. The device of claim 1 in combination with said apparatus for connecting a syringe to a vial containing a medicament, said apparatus being fitted on said collar and said fins.

* * * * *